(12) United States Patent
Osman

(10) Patent No.: US 8,540,772 B2
(45) Date of Patent: Sep. 24, 2013

(54) TRANSPEDICULAR, EXTRAPEDICULAR AND TRANSCORPOREAL PARTIAL DISC REPLACEMENT

(76) Inventor: Said G. Osman, Russellville, AL (US)

( * ) Notice: Subject to any disclaimer, the term of this patent is extended or adjusted under 35 U.S.C. 154(b) by 971 days.

(21) Appl. No.: 12/234,891

(22) Filed: Sep. 22, 2008

(65) Prior Publication Data

US 2009/0082870 A1    Mar. 26, 2009

Related U.S. Application Data

(60) Provisional application No. 60/973,899, filed on Sep. 20, 2007.

(51) Int. Cl.
*A61F 2/44* (2006.01)

(52) U.S. Cl.
USPC ........................................... 623/17.12

(58) Field of Classification Search
USPC ............................ 623/17.11–17.16; 606/246
See application file for complete search history.

(56) References Cited

U.S. PATENT DOCUMENTS

| | | | | | |
|---|---|---|---|---|---|
| 4,772,287 | A | * | 9/1988 | Ray et al. | 623/17.12 |
| 5,549,679 | A | * | 8/1996 | Kuslich | 623/17.12 |
| 5,571,189 | A | * | 11/1996 | Kuslich | 623/17.12 |
| 6,632,235 | B2 | * | 10/2003 | Weikel et al. | 606/192 |
| 2003/0195628 | A1 | * | 10/2003 | Bao et al. | 623/17.12 |
| 2004/0030392 | A1 | * | 2/2004 | Lambrecht et al. | 623/17.16 |
| 2004/0098015 | A1 | * | 5/2004 | Weikel et al. | 606/192 |
| 2005/0125066 | A1 | * | 6/2005 | McAfee | 623/17.16 |
| 2006/0253198 | A1 | * | 11/2006 | Myint et al. | 623/17.12 |
| 2007/0168041 | A1 | * | 7/2007 | Kadiyala | 623/17.16 |
| 2008/0039942 | A1 | * | 2/2008 | Bergeron | 623/17.16 |
| 2008/0249529 | A1 | * | 10/2008 | Zarda et al. | 606/93 |

* cited by examiner

*Primary Examiner* — Jan Christopher Merene
*Assistant Examiner* — Steven Cotroneo
(74) *Attorney, Agent, or Firm* — Nixon & Vanderhye P.C.

(57) ABSTRACT

A nucleus replacement mimics a native annulus in shape and function for use in partial disc arthroplasty. The nucleus replacement includes a jacket having a compartment, a first anchoring limb on one side of the compartment, and a second anchoring limb on an opposite side of the compartment. The jacket is insertable into a disc space through an operating channel in at least one of the vertebral pedicle and the vertebral body. A shock absorbing material is injectable into the compartment after installing the jacket into the disc space. The shock absorbing material has characteristics that absorb loads on the replacement.

23 Claims, 6 Drawing Sheets

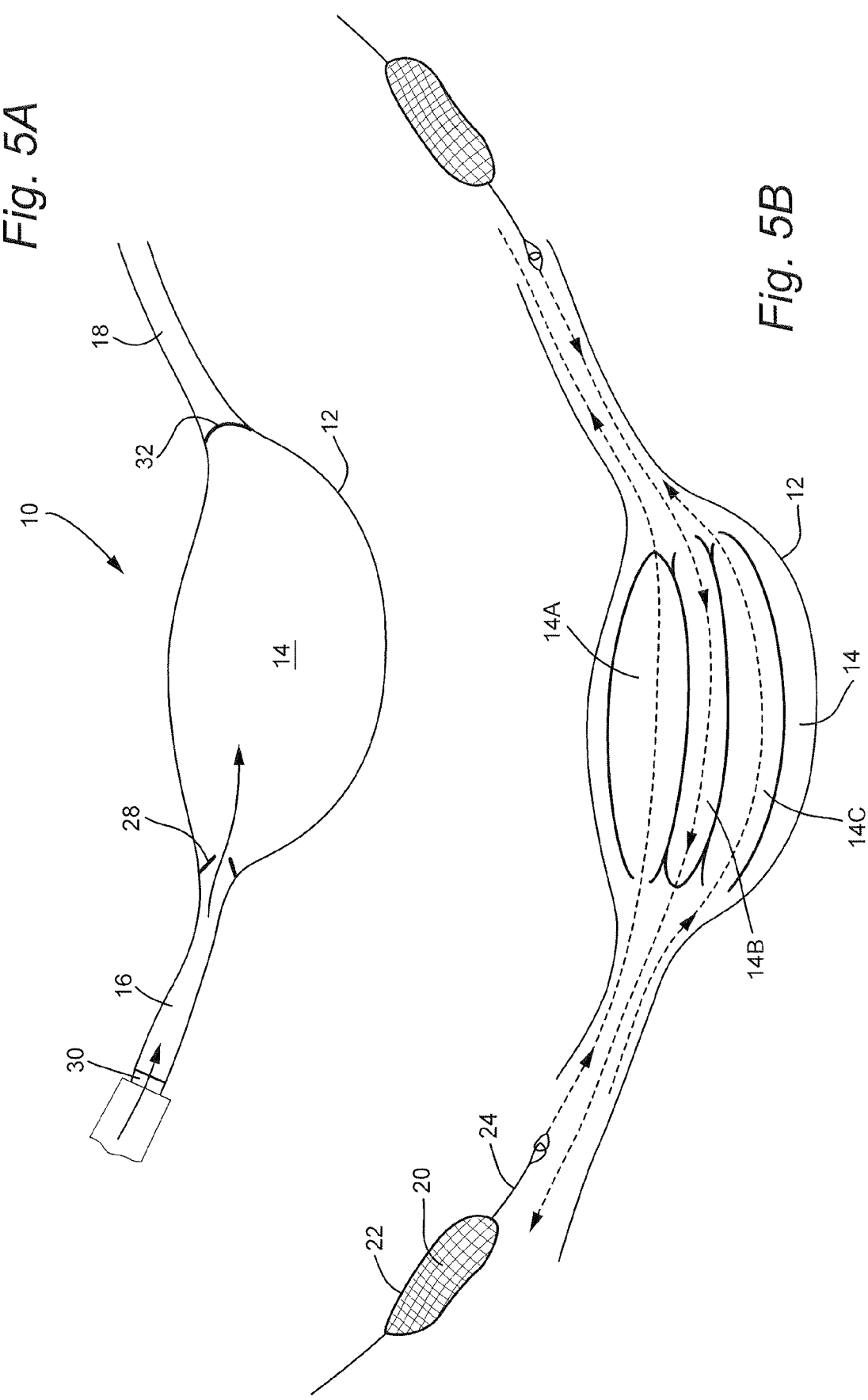

TRANSPEDICULAR, EXTRAPEDICULAR AND TRANSCORPOREAL PARTIAL DISC REPLACEMENT

CROSS-REFERENCES TO RELATED APPLICATIONS

This application claims the benefit of U.S. Provisional Patent Application Ser. No. 60/973,899, filed Sep. 20, 2007, the entire content of which is herein incorporated by reference.

STATEMENT REGARDING FEDERALLY SPONSORED RESEARCH OR DEVELOPMENT (NOT APPLICABLE)

BACKGROUND OF THE INVENTION

The invention relates to disc arthroplasty (or partial disc replacement) and, more particularly, to a nucleus replacement that mimics a native annulus in shape and function for use in partial disc arthroplasty.

The gold standard for the lumbar and cervical disc degeneration is currently fusion of the diseased motion-segment. The outcomes of the various fusion techniques have generally been satisfactory. Elimination of motion at a joint naturally produces stiffness and this in turn leads to transfer of forces normally absorbed by the motion-segments to the adjacent joints. As a result of the increased forces to which the adjoining joints are subjected, accelerated wear and tear takes place, setting the scene for arthritis at those joints. These observations have lead, therefore, to a search for alternative surgical treatments that would alleviate pain and restore function while preserving motion. Recently, a number of artificial disc prostheses have come into clinical use both in the lumbar spine and the cervicle spine. The results of these procedures, on medium term follow-ups, have been equivalent to fusion. Most of the devices for total disc replacement are performed anteriorly (through the belly) for the lumbar spine and the cervicle spine. The surgical trauma for the lumbar disc replacement is significant, and the approach has been associated with serious complications.

The current minimally invasive partial disc replacement devices are at experimental stages in the USA, and most have significant design flaws, notably instability of the devices in the disc spaces, and reliance on the already compromised annulus fibrosus to contain the devices. Furthermore, implantation of the current devices requires further violation of the annulus to implant the devices.

BRIEF SUMMARY OF THE INVENTION

The described embodiments endeavor to avoid the severe surgical trauma of the current partial disc arthroplasty by using minimally invasive techniques and also to avoid the pitfalls of partial disc replacements by avoiding further injury to the annulus and by utilizing intraosseous anchoring mechanisms to stabilize the device, instead of depending on a compromised annulus. The device and method avoid accessing the disc space through the disc wall and rather are designed to be inserted through one or both of the vertebral pedicle or vertebral body. The device and method utilize minimally invasive techniques for partial disc arthroplasty.

In an exemplary embodiment, a nucleus replacement mimics a native annulus in shape and function for use in partial disc arthroplasty. The nucleus replacement includes at least one jacket having a compartment, a first anchoring limb on one side of the compartment, and a second anchoring limb on an opposite side of the compartment. The at least one jacket is insertable into a disc space. A shock absorbing material is injectable into the compartment after installing the at least one jacket into the disc space. The shock absorbing material has characteristics that absorb loads on the replacement. In one arrangement, the replacement includes two jackets as an inner jacket and an outer jacket, where the outer jacket serves as a restraint for the nucleus replacement, and the inner jacket includes the compartment. In this context, the outer jacket may be formed of a material that encourages bone in-growth, such as one of a synthetic biologically active fabric and a synthetic biologically inert fabric. The compartment may comprise a plurality of compartments, which may be interconnected.

Preferably, the jacket is shaped as one of bean shaped, oval, and cylindrical. The shock absorbing material may be a liquid, a gelatinous osmotically active material, a fabric material, a biologic material or the like. The fabric material may be formed of a bundle of fibers contained within a sub-jacket insertable into the compartment. The bundle of fibers may include cylindrical fiber stacks.

One of the first anchoring limb and the second anchoring limb may be sealed, and the other of the first and second anchoring limbs may include a valve that provides external access to the compartment.

In a preferred arrangement, the replacement also includes a pair of intraosseous anchoring members cooperable with the first and second anchoring limbs, respectively. The intraosseous anchoring members serve to secure the nucleus replacement in the disc space. In this context, the intraosseous anchoring members may be bone plugs fixed into an end plate adjacent the disc space, screws that secure the first and second anchoring limbs in the disc space, suture anchors, or the like. The screws may be cannulated to serve as an injection port for the shock absorbing material.

In another exemplary embodiment, a method of inserting a nucleus replacement that mimics a native annulus in shape and function for use in partial disc arthroplasty includes the steps of (a) forming an operating channel through at least one of a vertebral pedicle and a vertebral body into a disc space; (b) cleaning the disc space with a disc reamer; (c) inserting at least one jacket including a compartment, a first anchoring limb on one side of the compartment, and a second anchoring limb on an opposite side of the compartment along the operating channel and into the disc space; and (d) injecting a shock absorbing material into the compartment after inserting the at least one jacket into the disc space, wherein the shock absorbing material includes characteristics that absorb loads on the replacement.

Step (c) may be practiced by controllably inserting the at least one jacket with vision guidance. The first and second anchoring limbs each may be provided with a radio-opaque marker, where step (c) may be practiced by controllably inserting the at least one jacket by sensing a position of the radio-opaque markers.

BRIEF DESCRIPTION OF THE DRAWINGS

These and other aspects and advantages will be described in detail with reference to the accompanying drawings, in which:

FIGS. 5A and 5B demonstrate implantation of the load-bearing device in the jacket.

DETAILED DESCRIPTION OF THE INVENTION

Figure 1A:
FIGS. 1A-1C show exemplary shapes of the nucleus replacement.
Figure 1B:
Figure 1C:
Figure 2A:
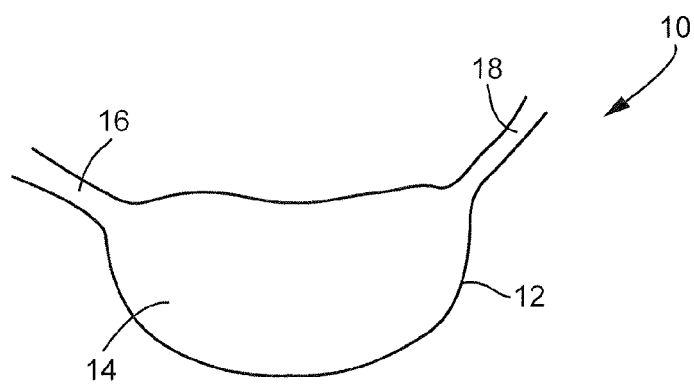
FIGS. 2A-2C illustrate configurations of the replacement jacket.
Figure 2B:
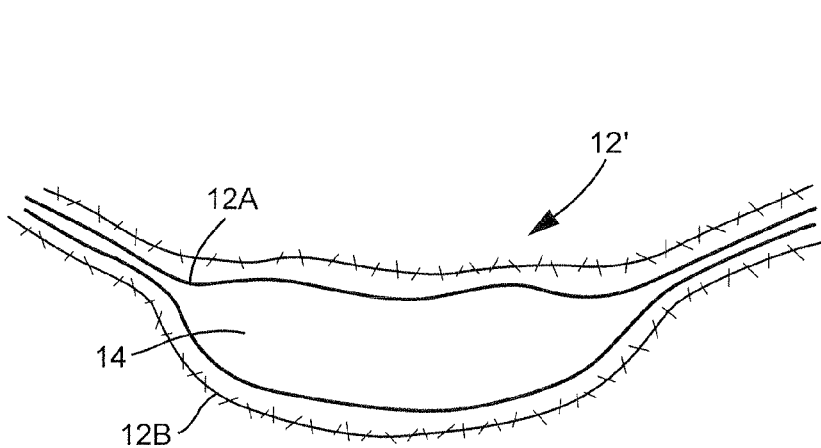

With reference to FIGS. 1A-1C and FIGS. 2A-2C, a nucleus replacement 10 mimics a native annulus in shape and function for use in partial disc arthroplasty. As shown in FIGS. 1A-1C, the replacement 10 can take numerous shapes including, without limitation, bean shaped, oval shaped, cylindrical shaped (or more accurately banana-shaped), and the like. The replacement 10 generally includes a jacket 12 that includes a compartment 14 and first and second anchoring limbs 16, 18. As described in more detail below, the anchoring limbs 16, 18 facilitate positioning of the jacket 12 in the disc space and enable the jacket 12 to be secured in the disc space. In FIG. 2A, the jacket 12 includes a single compartment 14. The jacket 12 may be formed of numerous suitable materials, including, without limitation, elastic or inelastic fabric, which may be pervious or impervious. FIG. 2B shows an embodiment utilizing a double jacket 12' including an inner jacket 12A and an outer jacket 12B. The outer jacket 12B serves as a restraint for the nucleus replacement 10, and the inner jacket 12A includes the compartment 14. The outer jacket 12B may be formed of or impregnated with a material that serves to encourage bone ingrowth. The outer jacket 12B is preferably formed of a synthetic, biologically active and/or inert fabric. The inner jacket 12A is preferably formed of an impervious synthetic material.

Figure 2C:
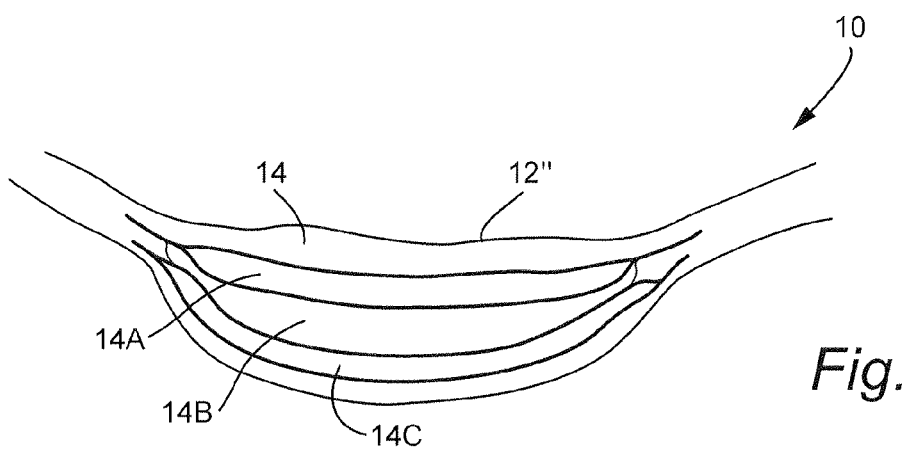

FIG. 2C shows yet another alternative for the jacket 12", which may be a single jacket as in FIG. 2A or a double jacket as in FIG. 2B. The compartment 14 is divided into a plurality of sub-compartments, e.g., 14A, 14B, 14C, which are preferably interconnected. The multi-compartment construction enables the replacement 10 to better fit the geometry of the spine. The multiple compartments 14A-14C are designed to allow distribution of forces across the disc in a uniform manner while maintaining the lordosis of the disc. The lordosis is achieved by making the anterior compartment larger than the posterior compartment.

Figure 3A:
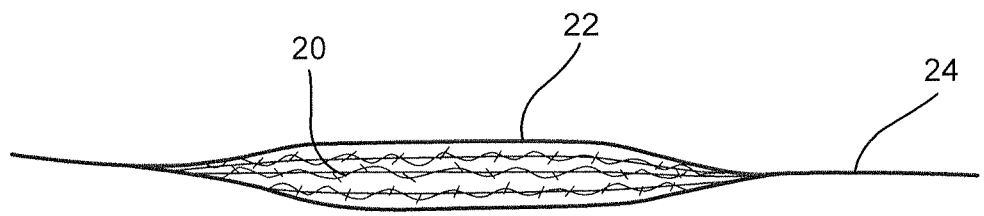
FIGS. 3A and 3B show exemplary load-bearing designs for insertion into the jacket.
Figure 3B:
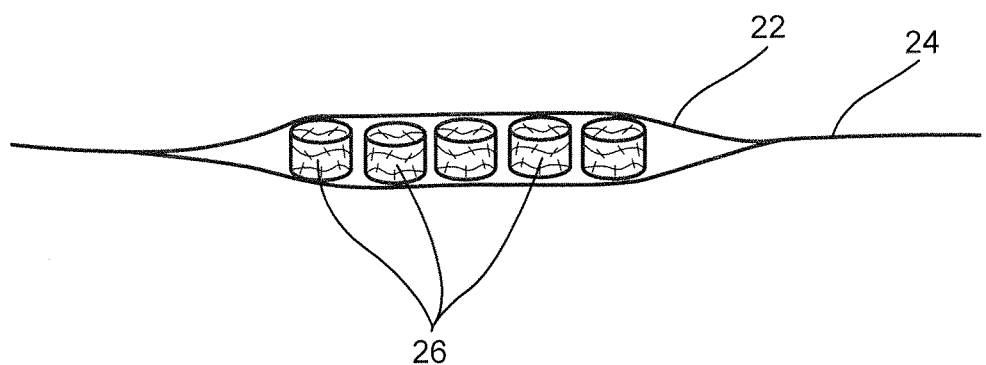

A shock-absorbing material/insert is injectable into the compartment 14 after installing the jacket 12 into the disc space. In the multi-compartment embodiment illustrated in FIG. 2C, with the compartments 14A-14C interconnected, the shock-absorbing material is preferably flowable between the compartments. Many materials are suitable for the shock-absorbing material, and it is preferred that the shock-absorbing material includes characteristics that absorb loads on the replacement 10. For example, the material may be a liquid, a gelatinous osmotically active material and/or a biological material. Alternatively, with reference to FIGS. 3A and 3B, the shock-absorbing material may comprise bundles of fabric or fibers 20 contained within a sub-jacket 22 including leading and trailing tails 24 that are used to pull the bundle into the jacket compartment 14. Alternatively, the sub-jacket 22 may include cylinders of fabric 26 that provide the shock-absorbing function. As would be appreciated by those of ordinary skill in the art, other materials and/or shapes of fabric and the like may be suitable, and the invention is not meant to be limited to the illustrated exemplary embodiments.

With reference to FIGS. 4A-4E, it is preferable to fix the replacement 10 in the disc space. Such fixation may be effected by fibrous ingrowth into the outer wall of the jacket 12 or bone ingrowth into the jacket 12. As noted, the jacket 12 or outer jacket 12B may be formed of a material that encourages bone or fibrous ingrowth. In a preferred construction, the replacement 10 is secured using intraosseous anchors that secure the anchoring limbs 16, 18 in an operating channel 34 through which the replacement 10 is inserted. In preparing the disc space, it is preferable to form an operating channel 34 through the vertebral pedicle VP and/or the vertebral body VB into the disc space (see FIG. 4A). After securing cannulas in the operating channel 34, the disc space can be cleaned using a disc reamer or the like through the cannulas. The replacement 10 is inserted through the operating channel 34, preferably under X-ray inspection. Alternatively or additionally, the first and second anchoring limbs 16, 18 may be provided with a radio-opaque marker to facilitate insertion of the replacement 10.

Figure 4A:
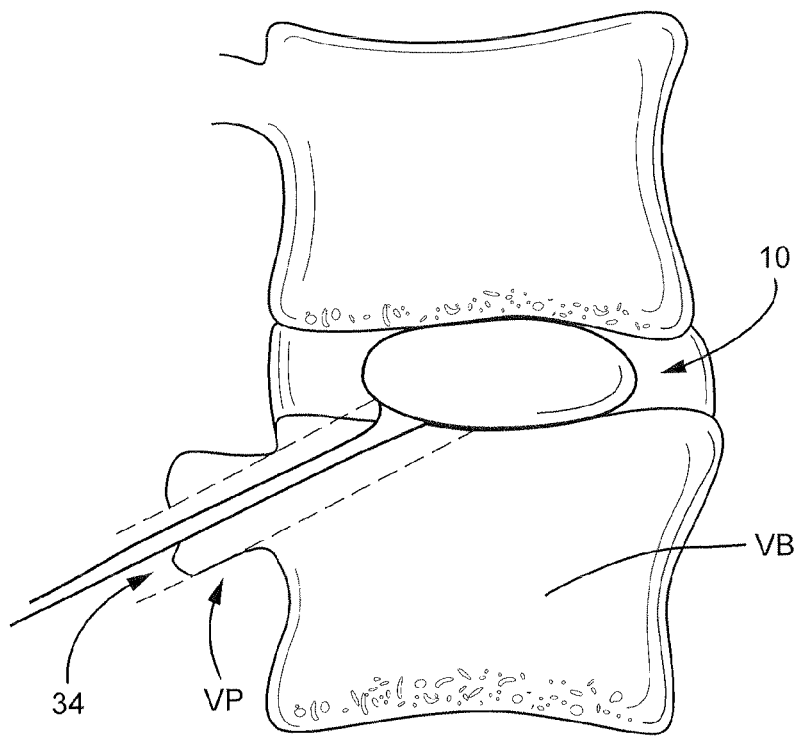
FIGS. 4A-4E show alternative configurations for anchoring the jacket in the disc space.
Figure 4B:
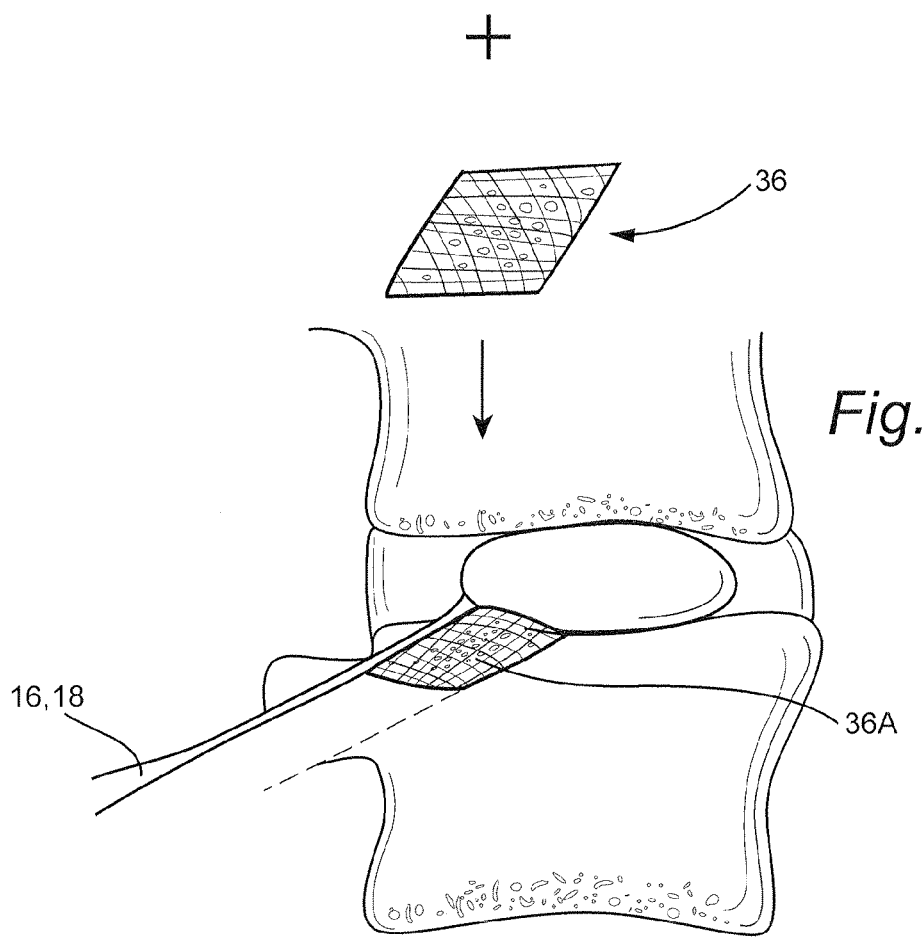
Figure 4C:
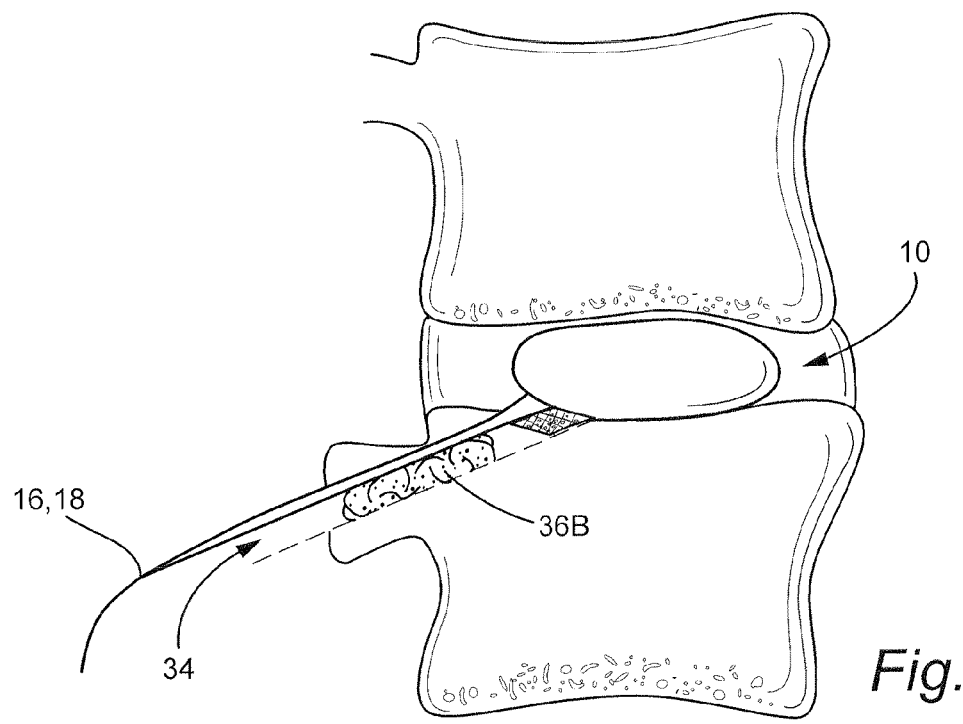
Figure 4D:
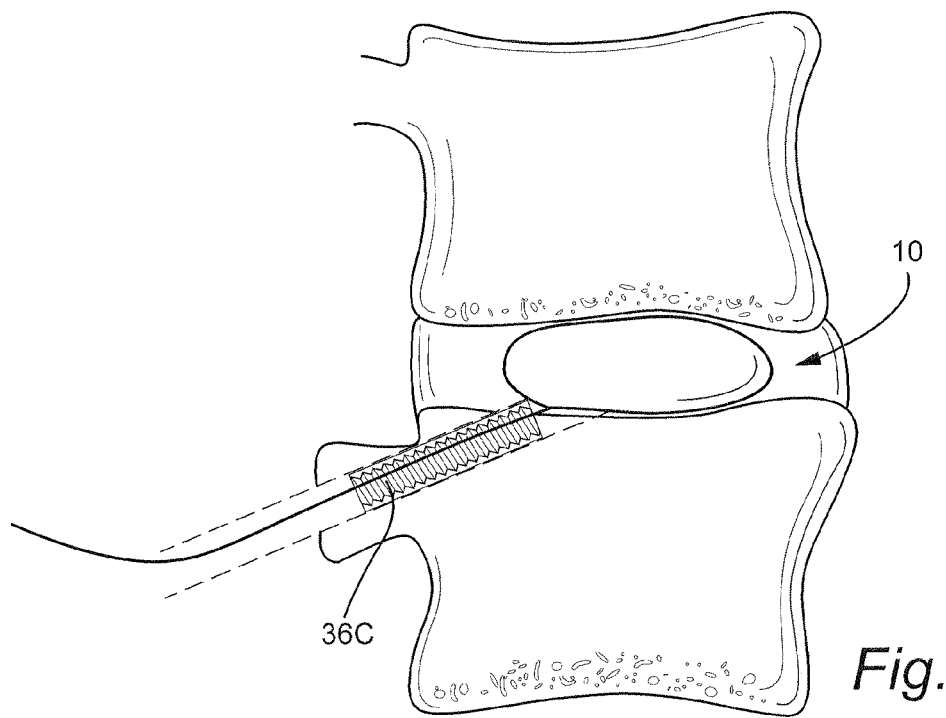
Figure 4E:
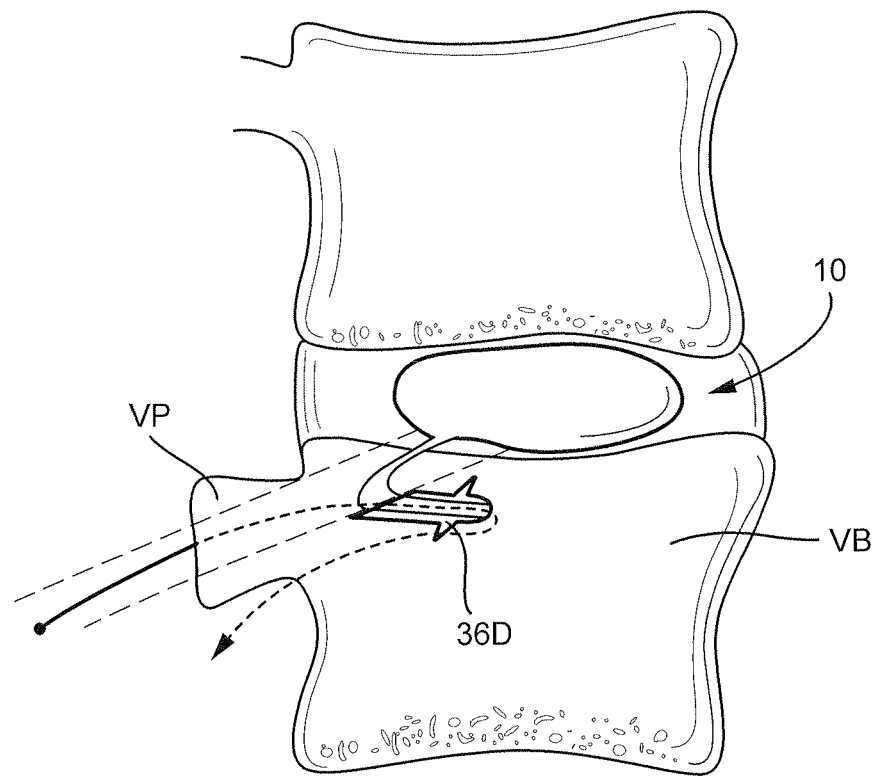

Once installed, the intraosseous anchors 36 can be inserted to secure the anchoring limbs 16, 18 via the operating channel 34. FIG. 4B shows a bone plug 36A disposed in the operating channel 34 to secure the anchoring limbs 16, 18. FIG. 4C illustrates the use of bone cement 36B inserted into the operating channel 34 for fixing the anchoring limbs 16, 18. FIG. 4D shows interferential screw fixation utilizing a screw 36C to secure the replacement 10 in the disc space. FIG. 4E shows the use of known suture anchors 36D in the vertebral body VB or vertebral pedicle VP.

With the anchoring structure as a screw 36C for interferential screw fixation, the screw 36C may be cannulated and used as a channel for access to the liquid filled replacement 10 for replenishment post-operatively at pre-defined intervals. The jacket 12 may be self-sealing in this design. Alternatively, the anchoring limbs 16, 18 may be fixed with a set-screw into the cannulated pedicle VP or intraosseous screw and used as a port for injectate.

The implantation approaches for the disc prosthesis or replacement 10 may be transpedicular, extrapedicular, transcorporeal, or transdiscal (for partial replacement of a surgical disc). The implantation technique is important for this minimally invasive device. Whether liquid, gel or fabric is used for the shock-absorbing material, the jacket 12 is inserted empty and subsequently armed with the shock-absorbing material in situ. As a consequence, a lesser amount of bone is removed in installing the replacement 10, thereby reducing the risk of fracture.

With reference to FIG. 5A, when liquids or osmotically active material is used as the shock-absorbing material, the replacement 10 may be additionally provided with a valve 28 at one end of the jacket 12 to allow inflow only of the fluid. In this arrangement, a nozzle 30 is provided at an end of the first anchoring limb 16 so that the material can be injected via a syringe. An opposite end of the jacket 12 adjacent the second anchoring limb 18 includes a seal 32 to prevent the liquid from escaping the compartment 14. The valve 28 also serves to prevent the extrusion of gelatinous material outside the nucleus compartment 14.

In using gel and fabrics as the shock-absorbing material, with reference to FIG. 5B, the shock-absorbing material can be housed in the mini- or sub-jackets 22 including the leading and trailing tails 24 at respective ends for pulling the device into the jacket 12. The side opposite the entrance is preferably sealed to prevent extrusion of the shock-absorbing material. In one design, openings in adjacent compartments 14A, 14B, 14C may be made to alternate between the right and left sides to facilitate insertion of the shock-absorbing material via the sub-jackets 22 in the multi-compartment embodiment.

The replacement structure and insertion method described facilitates minimally invasive partial disc replacements and partial disc arthroplasty, thereby avoiding the severe surgical trauma associated with current apparatus and techniques. The device and method also avoid the pitfalls of partial disc replacements by avoiding further injury to the annulus and by utilizing an anchoring mechanism to stabilize the device rather than depending on a compromised annulus. Moreover, insertion through the vertebral pedicle and/or vertebral body facilitates the minimally invasive technique.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A nucleus replacement that mimics a native annulus in shape and function for use in partial disc arthroplasty, the nucleus replacement comprising:
    at least one jacket including a compartment, a first anchoring limb on one side of the compartment, and a second anchoring limb on an opposite side of the compartment, the at least one jacket being insertable into a disc space with the first and second anchoring limbs on opposite lateral sides of the disc space;
    a shock absorbing material injectable into the compartment after installing the at least one jacket into the disc space, the shock absorbing material including characteristics that absorb loads on the replacement; and
    a pair of intraosseous anchoring members cooperable with the first and second anchoring limbs, respectively, the intraosseous anchoring members securing the nucleus replacement in the disc space,
    wherein one of the first anchoring limb and the second anchoring limb is sealed, and the other of the first and second anchoring limbs comprises a valve that provides external access to the compartment.

2. A nucleus replacement according to claim 1, comprising two jackets as an inner jacket and an outer jacket, the outer jacket serving as a restraint for the nucleus replacement, and the inner jacket including the compartment.

3. A nucleus replacement according to claim 2, wherein the outer jacket is formed of a material that encourages bone in-growth.

4. A nucleus replacement according to claim 3, wherein the outer jacket is formed of at least one of a synthetic biologically active fabric and a synthetic biologically inert fabric.

5. A nucleus replacement according to claim 2, wherein the compartment in the inner jacket comprises a plurality of compartments.

6. A nucleus replacement according to claim 1, wherein the compartment comprises a plurality of compartments.

7. A nucleus replacement according to claim 6, wherein the plurality of compartments are interconnected.

8. A nucleus replacement according to claim 1, wherein the jacket is shaped as one of bean shaped, oval, and cylindrical.

9. A nucleus replacement according to claim 1, wherein the shock absorbing material comprises a liquid.

10. A nucleus replacement according to claim 1, wherein the shock absorbing material comprises a gelatinous osmotically active material.

11. A nucleus replacement according to claim 1, wherein the shock absorbing material comprises a fabric material.

12. A nucleus replacement according to claim 11, wherein the fabric material comprises a bundle of fibers contained within a sub jacket insertable into the compartment.

13. A nucleus replacement according to claim 12, wherein the bundle of fibers comprises cylindrical fiber stacks.

14. A nucleus replacement according to claim 1, wherein the shock absorbing material comprises a biologic material.

15. A nucleus replacement according to claim 1, wherein the intraosseous anchoring members comprise bone plugs fixed into an end plate adjacent the disc space.

16. A nucleus replacement according to claim 1, wherein the intraosseous anchoring members comprise screws that secure the first and second anchoring limbs in the disc space.

17. A nucleus replacement according to claim 16, wherein the screws are cannulated and define an injection port for the shock absorbing material.

18. A nucleus replacement according to claim 1, wherein the intraosseous anchoring members comprise suture anchors.

19. A method of inserting a nucleus replacement that mimics a native annulus in shape and function for use in partial disc arthroplasty, the method comprising:
    (a) forming an operating channel through at least one of a vertebral pedicle and a vertebral body into a disc space;
    (b) cleaning the disc space with a disc reamer;
    (c) providing at least one jacket including a compartment, a first anchoring limb on one side of the compartment, and a second anchoring limb on an opposite side of the compartment, wherein one of the first anchoring limb and the second anchoring limb is sealed, and the other of the first and second anchoring limbs comprises a valve that provides external access to the compartment;
    (d) inserting the at least one jacket along the operating channel and into the disc space; and
    (e) injecting a shock absorbing material into the compartment after inserting the at least one jacket into the disc space, wherein the shock absorbing material includes characteristics that absorb loads on the replacement.

20. A method according to claim 19, wherein step (d) is practiced by controllably inserting the at least one jacket with vision guidance.

21. A method according to claim 19, wherein the first and second anchoring limbs each comprise a radio-opaque marker, and wherein step (d) is practiced by controllably inserting the at least one jacket by sensing a position of the radio-opaque markers.

22. A nucleus replacement that mimics a native annulus in shape and function for use in partial disc arthroplasty, the nucleus replacement comprising:
    a jacket including a plurality of interconnected compartments, a first anchoring limb on one side of the compartment, and a second anchoring limb on a lateral opposite side of the compartment, the jacket being insertable through an operating channel formed in at least one of a vertebral pedicle and a vertebral body into a disc space;
    a shock absorbing material injectable into the compartment through one of the first and second anchoring limbs after installing the jacket into the disc space, the shock absorbing material including characteristics that absorb loads on the replacement; and
    a pair of anchor members affixable in the operating channel that secure the first and second anchoring limbs and thereby secure the jacket in the disc space,
    wherein one of the first anchoring limb and the second anchoring limb is sealed, and the other of the first and second anchoring limbs comprises a valve that provides external access to the compartment.

23. A method of inserting a nucleus replacement that mimics a native annulus in shape and function for use in partial disc arthroplasty, the method comprising:

(a) forming an operating channel through a vertebral pedicle into a disc space;
(b) securing cannulas in the operating channel;
(c) cleaning the disc space with a disc reamer through the cannulas;
(d) providing a jacket including a plurality of interconnected compartments, a first anchoring limb on one side of the compartment, and a second anchoring limb on an opposite side of the compartment, wherein one of the first anchoring limb and the second anchoring limb is sealed, and the other of the first and second anchoring limbs comprises a valve that provides external access to the compartment;
(e) inserting the jacket along the operating channel and into the disc space;
(f) injecting a shock absorbing material into the compartment after inserting the jacket into the disc space, wherein the shock absorbing material includes characteristics that absorb loads on the replacement; and
(g) anchoring the jacket in the disc space using the first and second anchoring limbs.

\* \* \* \* \*